(12) United States Patent
Kwartowitz et al.

(10) Patent No.: US 9,615,815 B2
(45) Date of Patent: Apr. 11, 2017

(54) DEVICES THAT COOPERATE WITH ULTRASOUND PROBES FOR MUSCOSKELETAL EVALUATIONS AND RELATED SYSTEMS AND METHODS

(71) Applicant: Clemson University, Anderson, SC (US)

(72) Inventors: David Kwartowitz, Pendleton, SC (US); Erika Trent, Myrtle Beach, SC (US); Fuad Mefleh, Westminster, SC (US); Vipul Pai Raikar, Margao (IN); Delphine Dean, Central, SC (US)

(73) Assignee: Clemson University Research Foundation, Clemson, SC (US)

( * ) Notice: Subject to any disclaimer, the term of this patent is extended or adjusted under 35 U.S.C. 154(b) by 287 days.

(21) Appl. No.: 14/034,756

(22) Filed: Sep. 24, 2013

(65) Prior Publication Data
US 2014/0094701 A1 Apr. 3, 2014

Related U.S. Application Data

(60) Provisional application No. 61/707,312, filed on Sep. 28, 2012.

(51) Int. Cl.
*A61B 8/14* (2006.01)
*A61B 8/08* (2006.01)
*A61B 8/00* (2006.01)

(52) U.S. Cl.
CPC ............ *A61B 8/485* (2013.01); *A61B 8/0875* (2013.01); *A61B 8/4209* (2013.01); *A61B 8/429* (2013.01)

(58) Field of Classification Search
CPC ....................................................... A61B 8/44
See application file for complete search history.

(56) References Cited

U.S. PATENT DOCUMENTS

| | | | |
|---|---|---|---|
| 5,152,294 A | 10/1992 | Mochizuki et al. | |
| 5,897,503 A | 4/1999 | Lyon et al. | |
| 5,897,510 A | 4/1999 | Keller et al. | |
| 6,322,506 B1 | 11/2001 | Nagai et al. | |
| 6,511,427 B1 | 1/2003 | Sliwa, Jr. et al. | |
| 6,569,098 B2 | 5/2003 | Kawchuk | |
| 6,705,813 B2 | 3/2004 | Schwab | |
| 7,914,456 B2 | 3/2011 | Osaka et al. | |
| 2007/0205785 A1* | 9/2007 | Nilsson | A61B 8/00 600/459 |
| 2007/0232916 A1* | 10/2007 | Waki | 600/444 |

(Continued)

OTHER PUBLICATIONS

Garra et al. "Elastography of Breast Lesions: Initial Clinical Results", *Radiology*, vol. 202, Issue 1, Jan. 1997, 79-86.

(Continued)

*Primary Examiner* — James Kish
(74) *Attorney, Agent, or Firm* — Myers Bigel, P.A.

(57) ABSTRACT

Adaptors for ultrasound probes can have an adaptor body can have an open lower end that allows a distal end of the ultrasound probe to extend therethrough to contact skin of a patient. The adaptor can include a plurality of spaced apart resilient members held by the adaptor body that, in operation, are able to change in length such that the resilient members translate from a first longer length to a second shorter length when the probe applies compressive force to the target tissue.

17 Claims, 15 Drawing Sheets

(56) References Cited

U.S. PATENT DOCUMENTS

| | | | |
|---|---|---|---|
| 2007/0244390 A1* | 10/2007 | Matsumura | A61B 8/08 600/437 |
| 2007/0276238 A1* | 11/2007 | Sudol | B06B 1/0633 600/437 |
| 2009/0306515 A1* | 12/2009 | Matsumura et al. | 600/459 |
| 2011/0040187 A1* | 2/2011 | Matsumura | A61B 5/6843 600/443 |
| 2012/0172710 A1 | 7/2012 | Anthony et al. | |
| 2014/0039314 A1* | 2/2014 | Stoianovici et al. | 600/439 |

OTHER PUBLICATIONS

Cochlin et al. "Elastography in the Detection of Prostatic Cancer", *Clinical Radiology*, 2002, 57:1014-1020.

Fromageau et al. "Characterization of PVA Cryogel for Intravascular Ultrasound Elasticity Imaging", *IEEE Transactions on Ultrasonics, Ferroelectrics, and Frequency Control*, vol. 50, No. 10, Oct. 2003, 1318-1324.

Fromageau et al. "Estimation of Polyvinyl Alcohol Cryogel Mechanical Properties with Four Ultrasound Elastography Methods and Comparison with Gold Standard Testings", *IEEE Transactions on Ultrasonics, Ferroelectrics, and Frequency Control*, vol. 54, No. 3, Mar. 2007, 498-508.

Garra et al. "Elastography of breast lesions: initial clinical results", *Radiology*, Jan. 1997, 202(1):79-86 (Abstract Only).

Trent et al. "Assessment and Characterization of in situ Rotator Cuff Biomechanics", *Proc. SPIE, vol. 8672 Medical Imaging 2013: Biomedical Applications in Molecular, Structural, and Functional Imaging*, Mar. 29, 2013.

Whittaker et al. "Rehabilitative Ultrasound Imaging: Understanding the Technology and Its Applications", *Journal of Orthopaedic & Sports Physical Therapy*, Aug. 2007, vol. 37, No. 8, pp. 434-449.

\* cited by examiner

FIGURE 12. ULTRASOUND IMAGE OF ECOFLEX30. THE ARROW INDICATES THE BUBBLES INCREASING THE ATTENUATION OF THE ULTRASOUND SIGNAL

STRESS-STRAIN CURVE TO DETERMINE THE YOUNG'S MODULUS FOR PVA-C PHANTOM

DEVICES THAT COOPERATE WITH ULTRASOUND PROBES FOR MUSCOSKELETAL EVALUATIONS AND RELATED SYSTEMS AND METHODS

RELATED APPLICATIONS

This application claims the benefit of and priority to U.S. Provisional Application Ser. No. 61/707,312, filed Sep. 28, 2012, the contents of which are hereby incorporated by reference as if recited in full herein.

FIELD OF THE INVENTION

The present invention relates to ultrasound elastography.

BACKGROUND

Rotator cuff disease impacts over 50% of the population over age 60, with a range of severity from partial thickness through total rupture. This disease is believed to be degenerative and will continue to worsen if there is no intervention. It is currently believed that the transition from type I to type II collagen in the tendenous tissue may contribute to rotator cuff disease. In current clinical practice, treatment decisions are frequently made through subjective assessment of pain and range of motion combined with qualitative assessment of X-ray or ultrasound images. Treatment of disease may include physical therapy, surgery, or a combination of both. Patient history, physical examination, and medical imaging are used to determine course of treatment. However, currently there is little objective data upon which to determine disease progression or injury, which can lead to unnecessary, inappropriate, painful, and expensive treatments that may or may not benefit the patient. Indeed, the final determination of the best course of action is typically at the subjective discretion of the clinician, and is often based on personal experiences as opposed to quantitative standards.

Ultrasound can visualize and assess subsurface tissues while posing extremely low risk to the patient and practitioner. Techniques in ultrasound acquisition and post-processing have been used for the non-invasive determination of tissue mechanical properties. This combined process has become known as ultrasound elastography, and has shown much promise in the diagnosis of disease and disorder. See, e.g., Garra et al., Elastography of breast lesions: initial clinical results, Radiology 1997; 202:79-86; Whittaker et al., Rehabilitative ultrasound imaging: understanding the technology and its applications; J Orthop Sports Phys Ther 2007; 37: 434-49; and Cochlin et al., Elastography in the detection of prostatic cancer; Clinical Radiology 2002; 57: 1014-20.

Despite the foregoing, there remains a need for alternate, cost effective and easy-to-use devices and systems that provide objective measurements of tissue elasticity and/or stiffness.

SUMMARY OF EMBODIMENTS OF THE INVENTION

Embodiments of the present invention provide devices, circuits, and systems that provide calculated measurements of tissue stiffness using ultrasound images of tissue compression and synchronized force measurements used to cause the tissue compression.

Embodiments of the invention are directed to adaptors for ultrasound probes. The adaptors include an adaptor body releasably attachable to an outer portion of an ultrasound probe. The adaptors also include at least one force transducer configured to obtain a force measurement of force applied to target tissue by a respective ultrasound probe.

The adaptor body can have an open lower end that allows a distal end of the ultrasound probe to extend therethrough to contact skin of a patient. The adaptor can include a plurality of spaced apart resilient members held by the adaptor body that, in operation, are able to change in length such that the resilient members translate from a first longer length to a second shorter length when the probe applies compressive force to the target tissue.

The adaptor body can include an open frame body with upper and lower substantially rigid members. The adaptor body can hold a plurality of spaced apart translating members between the upper and lower substantially rigid members. The lower member can be configured to contact skin of a patient and translate toward the upper member thereby forcing the translating members toward the upper member thereby retracting or compressing the translating members in response to inward compression of the target tissue by the ultrasound probe.

The adaptor body can include a case that substantially encloses at least one side of the probe body. The adaptor body can hold a plurality of spaced apart translating members that retract or compress in response to inward compression of the target tissue by the ultrasound probe.

The adaptor can include a plurality of translating members held by the adaptor body. The translating members can reciprocate in response to manual inward compression and outward release of compression of the target tissue by the ultrasound probe.

The probe has a distal end with a skin contacting surface having a surface area. The at least one force sensor can include at least one elongate flexible sensor that extends orthogonal to a plane extending parallel to the distal end surface.

The adaptor body can have an open lower end that allows the distal end of the ultrasound probe to extend therethrough to contact skin of a patient. The adaptor can further include a plurality of spaced apart resilient members held by the adaptor body in communication with the at least one force sensor.

The adaptor can be in combination with a module that is in communication with the adaptor and the ultrasound probe that can be configured to generate at least one of: (i) force measurement data to metadata of ultrasound images; and (ii) generate a color coded overlay or mask image of tissue stiffness based on stress and strain data; and (iii) compute stress, strain and Elastic Modulus for each segmented region of the target tissue.

The adaptor can be in combination with a module that can be configured to synchronize an ultrasound image with a force measurement by the adaptor, calculate a stress using the force measurement and a surface area of a distal end of the probe, identify a change in length from a baseline associated with an initial at rest or uncompressed tissue thickness length of the target tissue to a compressed tissue length associated with the applied force of the target tissue and calculate strain and Elastic Modulus of the target tissue.

The adaptor can be in communication with a display configured to display a color coded overlay of tissue stiffness of the target tissue using force measurement data from the adaptor. A display can be in communication with the module that shows the color coded overlay of tissue stiffness.

The adaptor body can include an open frame body with upper and lower substantially rigid members. The adaptor body can hold a plurality of spaced apart upwardly extending rods, with opposing end portions thereof attached to the upper and lower substantially rigid members. The adaptor body can also hold at least one coil spring surrounding each rod and residing between the upper and lower substantially rigid members. The at least one force sensor can include an elongate flex sensor that extends substantially parallel to and adjacent the coil spring(s) of at least one of the rods. The lower member can be configured to contact skin of a patient and translate toward the upper member thereby compressing the coil springs toward the upper member in response to inward compression of the target tissue by the ultrasound probe.

Still other embodiments are directed systems for providing data for evaluating soft tissue. The systems include a circuit that (i) obtains force measurements from an adaptor releasably attached to an ultrasound probe that defines forces applied by an ultrasound probe to obtain respective compressed tissue ultrasound images, a force measurement synchronized with a corresponding ultrasound image; (ii) calculates stress using the force measurement and a probe distal end, patient-contact surface area; (iii) segments obtained ultrasound images to identify a change in length between a baseline length of the target tissue to a length associated with the compressed target tissue; (iv) calculates strain based on the baseline length and change in length; and (v) calculates Young's Modulus using the calculated stress and strain.

The circuit can (electronically) attach the force measurements as metadata with image data of the ultrasound images for electronic storage in a PACS.

The circuit can be in communication with a display and can provide a color-coded overlay of tissue stiffness of the target tissue to a display based on the calculated Modulus.

Other aspects of the invention are directed to methods of evaluating muscoskeletal tissue. The methods include: (a) manually pressing an ultrasound probe against skin of a patient to obtain ultrasound images of compressed target tissue, the ultrasound probe having a distal end with a patient contact surface having a surface area; (b) obtaining an ultrasound image of the compressed target tissue; (c) electronically obtaining a force measurement from an adaptor releasably attached to the ultrasound probe; (d) electronically calculating stress using the force measurement and the probe distal end surface area; (e) electronically segmenting the obtained ultrasound image to identify a change in length between a baseline length of the target tissue to a length associated with the compressed target tissue; (f) electronically calculating strain based on the baseline length and change in length; (g) electronically calculating Young's Modulus using the calculated stress and strain; and (h) electronically providing the calculated Modulus to a display.

The method may also include synchronizing the force measurement with the corresponding ultrasound image and attaching the force measurement as metadata with image data of the ultrasound image for electronic storage in a PACS.

The method can include generating a color-coded overlay of tissue stiffness of the target tissue.

The target tissue can be associated with a rotator cuff of the patient.

The method can include repeating the steps at a second point in time and comparing at least one of the calculated Modulus, stress and/or strain to monitor disease progress.

Embodiments of the invention can be used for screening youth or adult athletes or students or monitoring for changes in tissue stiffness for earlier or more reliable evaluation of tissue status or change.

Embodiments of the invention can be used to evaluate tissue stiffness associated with the rotator cuff to assess a likelihood of injury or disease and the need or lack of need for surgical intervention.

Embodiments of the invention can be used to differentiate the difference between type I and type II collagen within the rotator cuff and to be able to assess the impact this difference may have on tissue injury or disease.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Other systems and/or methods according to embodiments of the invention will be or become apparent to one with skill in the art upon review of the following drawings and detailed description. It is intended that all such additional systems, methods, and/or devices be included within this description, be within the scope of the present invention, and be protected by the accompanying claims.

BRIEF DESCRIPTION OF THE DRAWINGS

The patent or application contains at least one drawing executed in color. Copies of this patent or patent application publication with color drawings will be provided by the Office upon request and payment of the necessary fee.

Other features of the present invention will be more readily understood from the following detailed description of exemplary embodiments thereof when read in conjunction with the accompanying drawings.

DETAILED DESCRIPTION OF EMBODIMENTS OF THE INVENTION

Figure 1:
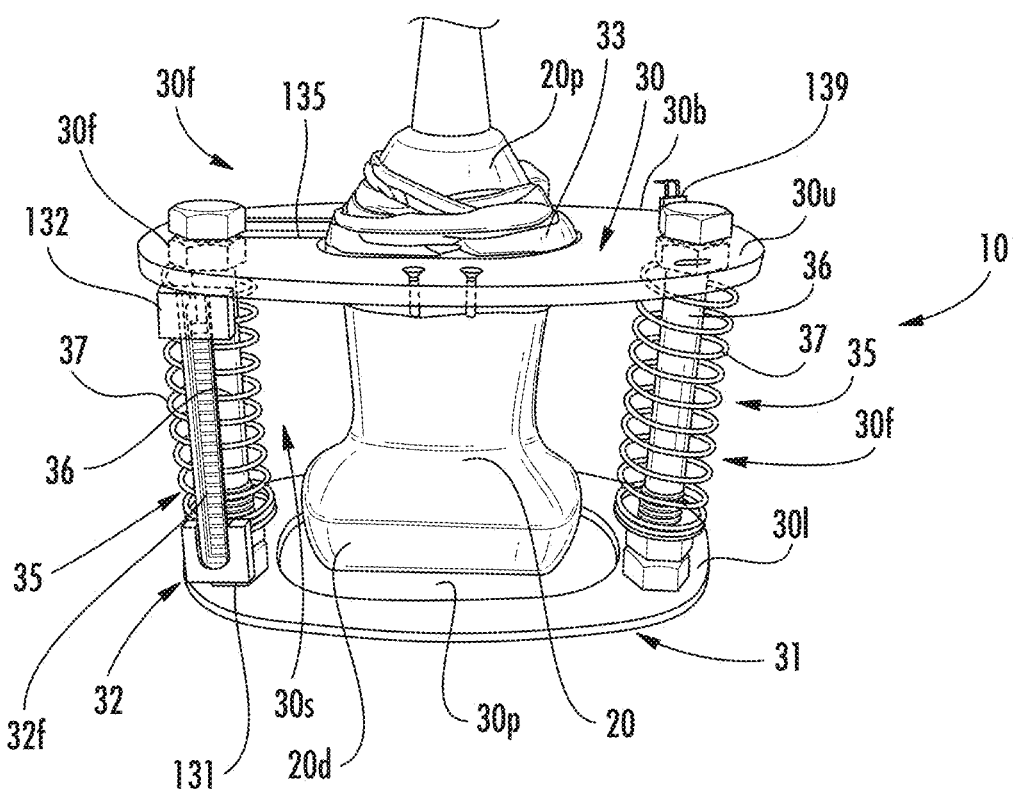
FIG. 1 is a front perspective view of an exemplary adaptor for an ultrasound probe according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. One or more features shown and discussed with respect to one embodiment may be included in another embodiment even if not explicitly described or shown with another embodiment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "about" means that the recited number or value can vary by +/−20%.

Embodiments of the invention are particularly suitable for human uses and/or veterinary uses for muscoskeletal evaluations including stiffness (elasticity) measurements of tendonous or soft tissues.

The term "stiffness" is used interchangeably with "elasticity" as measures of the same mechanical property of tissue.

The term "ultrasound systems" is well known and includes any commercially available system including, but not limited to: Acuson's Sequoia® and Aspen™ platforms; Philips/ATL's HDI® platforms; General Electric's LOGIQ™ platforms; Toshiba's PowerVision™ platforms;

Hewlett-Packard's Sonos™ platforms; Siemen's Sonoline® and Elegra™ platforms; and the like. The instant invention does not depend on the specific type of ultrasound platform used. The term "ultrasound probe" refers to the part of the ultrasound system device with the transducer/transducer array that contacts a patient to obtain ultrasound imaging data.

The term "color coded" means that a defined tissue stiffness or tissue stiffness range is associated with a defined color, hue or opacity of a color so that an image with different colors, hues or opacities or the same can visually illustrate common and different stiffness values. The color coded image can be integrated into an ultrasound image and/or may be provided as an overlay on the image of the FOV (field of view) tissue. A User Interface (UI) such as a Graphic User Interface (GUI) can be in communication with a display circuit and configured to allow a user to selectively apply the color coding onto the tissue. Where an overlay is used, the UI may also allow a user to increase the intensity from hidden to dominant over the ultrasound image.

Turning now to the figures, FIG. 1 illustrates an assembly 10 with an ultrasound probe 20 and an applied-force measurement adaptor 30. In some embodiments, the adaptor 30 is releasably attachable to the probe 20. The adaptor 30 can be configured to attach to probes 20 in clinical use, e.g., for retrofit of or use with existing systems 50 (FIG. 4) in various field sites or clinical sites.

The adaptor 30 can cooperate with the probe 20 to perform tissue elastography. The adaptor 30 can measure the force applied by an ultrasound probe 20 during ultrasound imaging. This adaptor 30 can be instrumented with at least one force transducer 32 (also interchangeably called a force sensor). The adapter 30 can include a connector 139 to the sensor 32. From the known dimensions of the ultrasound probe 20 applying the force, the stress at the tissue surface can be computed. Typical applied forces are between about 0-6 $lb_f$ such as between about 0.25-5 $lb_f$.

The adaptor 30 can also include at least one angular and acceleration sensor. These sensors can allow for the (typically electronic) computation of the force applied by the ultrasound probe 20, resulting joint torsion, and acceleration.

Figures 2A, 2B:
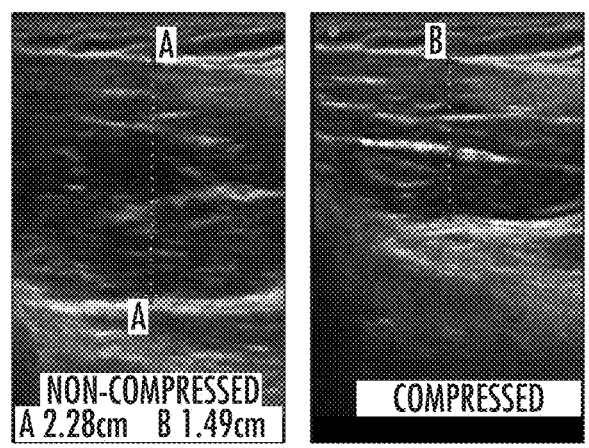
FIGS. 2A and 2B are ultrasound images of non-compressed and compressed tissue, respectively.

FIGS. 2A and 2B are examples of a typical ultrasound image of the rotator cuff showing the humeral head and insertion of the bicep. The tissue boundaries are clearly visible. FIG. 2A shows no compression and FIG. 2B shows moderate compression. The tissue boundaries are visible and the change in tissue thickness due to the compression can be electronically identified and computed.

Ultrasound images allow for the visualization of subsurface tissue boundaries in a real-time sense. These images can be processed to compute the deformation due to the applied stress. From the (real-time) tissue deformation with a calculated force, the tissue strain can be calculated. Using the tissue stress and strain, the tissue compressive modulus can then be computed and compared to determine tissue composition. The elasticity of a material is defined by a quantity known as Young's Modulus (E), which is a function of stress (a) and strain (c). Stress is a property of an applied force (F) applied over a surface area (A), while strain is a change in the length of the material (l) as a function of its original length ($l_o$). This relationship is shown in Equation 1, in which local elasticity in tissues can be computed given a known transducer area (A) and the measurement of the applied force (F) at the distal end of the probe for the ultrasound transducer. The length l and change in length can be measured from the resulting ultrasound images.

$$\sigma = \frac{F}{A} \quad \varepsilon = \frac{\Delta \ell}{\ell_o} = \frac{\ell - \ell_o}{\ell_o} \quad E = \frac{\sigma}{\varepsilon} = \frac{(F/A)}{(\ell - \ell_o/\ell_o)} = \frac{F(\ell_o)}{A(\ell - \ell_o)} \quad \text{Eqn. 1}$$

Referring again to FIG. 1, as noted above, the adaptor 30 includes at least one force transducer 32. A respective force sensor 32 can include any suitable force transducer. In the embodiment shown, the force sensor 32 includes a flex sensor 32f.

In some embodiments, the adaptor 30 includes at least one upstanding translating member 35. The sensor 32 can run parallel to at least one of the at least one translating member 35. The at least one translating member 35 can include a resilient member 37. The sensor 32 can be oriented to run substantially parallel to the axial direction of the resilient member 37. The sensor 32 can comprise a flex sensor 32f which can have a length that is at least a major portion of a length of the translating member 35, e.g., the resilient member 37, but less than the entire length in an uncompressed or ready to use configuration.

The wire connector 139 of the force sensor 32 can reside on an outer surface of the adaptor body 30b for ease of access. In other embodiments, the connector 139, where used, can be held inside the adaptor 30 and wiring access can be via a harness. The at least one translatable member 35 can be attached (directly or indirectly) to a lower surface 31 of the adapter 30 to be able to move away from the tissue and distal end of the probe 20d.

Other force sensors may be used, including, for example, a load cell sensor or a linear variable differential transducer (LVDT) that can be used within a load cell to measure the displacement of the resilient member 37. However, as is known to those of skill in the art, other transducers/sensors 32 may be used, including, for example, piezoelectric transducers. Examples of a suitable commercially available flex sensor includes the Flex Sensor FS-L-0055-253-ST, from Spectra Symbol, Salt Lake City, Utah.

Figure 5A:
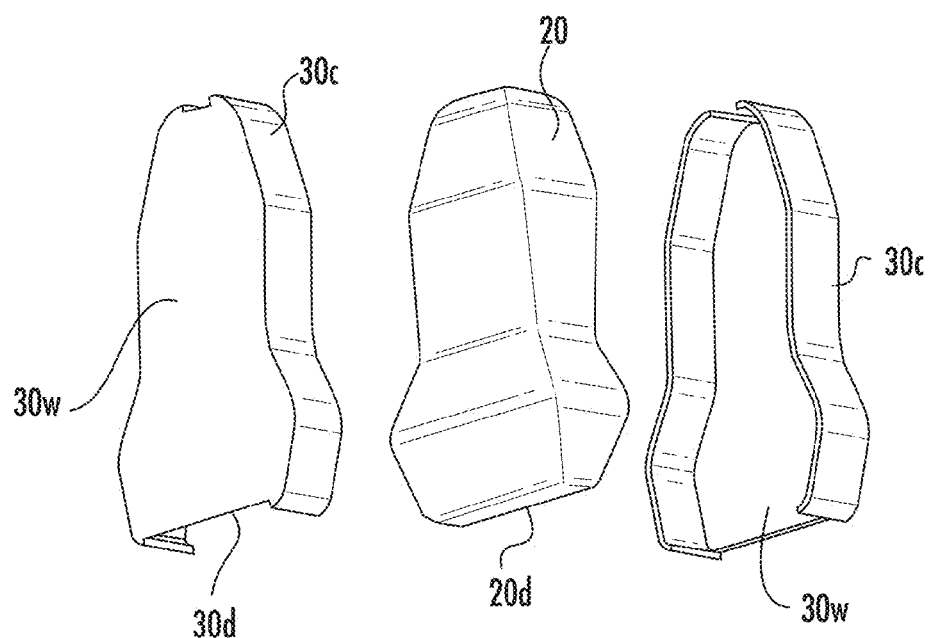
FIG. 5A is an exploded view of another embodiment of an exemplary adaptor body according to embodiments of the present invention.

An alternative embodiment, which may be particularly suitable for the embodiment shown in FIG. 5A, can employ one or more load cell sensors, such as the Omega, LCL-005, from Omega Inc., Stamford, Conn.

For the calculations described herein, the area (A) of the probe 20 can be selected based on a reference brochure, website or manual or electronic look-up table or other chart or data of different manufacturer probes and associated sizes (area).

Also in FIG. 1, the adapter 30 is shown as comprising two laterally spaced apart upstanding translating members 35 that include respective shafts 36 that reside across from each other on either side of an open space 30s that holds the probe 20. However, additional such members 35, e.g., front and back as well as side to side positions, can be used to help stabilize, distribute or equalize the translational response of the surface 31 to the probe applied force, which may be appropriate for providing reliable measurements in some embodiments.

In the embodiment shown in FIG. 1, one of the translating members 35 includes an upstanding member 131 attached to the upper surface of a patient contacting surface 31 (shown on the left side of the adaptor 30) that is aligned with a downwardly extending (static) member 132 residing above the member 131. The lower member 131 moves up in response to downward compression of the probe 20 against a patient and the flex sensor 32f defines the applied force.

In other embodiments, a graduated scale can be used with an optical reader or encoder can define the applied force based on a correlation of distance between the two members 131, 132 to an applied force.

In some embodiments, one translatable member 35 can be the master and another one or more can be the slave member. The master translatable member 35 can reside proximate the sensor 32. The slave member 35 can provide structural stability without providing any force measurements. In other embodiments, two or more master translatable members 35 can be used, each with sensors 32 and an average (or mean) force can be calculated using two or more force measurements of the applied force.

In some embodiments, the translatable members 35 can be attached, directly or indirectly, to a bottom patient contacting surface 31 that is in communication with a plurality of rods 36. Each rod 36 can be in communication with at least one resilient member 37. In operation, the surface 31 presses against external skin of the patient in response to a user pushing the probe 20 against the patient to compress internal tissue. The adaptor 30 (via the surface 31) then pushes the translatable member(s) 35 linearly away from the patient toward the proximal end of the probe 20p.

The translatable member(s) 35 can include a resilient (elastomeric) or other member such as, for example, gas cylinders/dampers that linear translate a known distance for a defined applied force.

FIG. 1 illustrates the translatable members 35 comprise a lower member 131, rod 36 and resilient member 37 that can be attached to or reside proximate the lower upwardly facing surface of the probe adapter 30 as shown. Although as one coil spring for each rod, more than one coil spring may be used of the same or different spring factors. Where springs are used, they can typically have a spring factor "K" in the range of between about 1000 N/M up to about 5000 N/M. In some embodiments, K can be about 1000 N/M, about 2000 N/M, about 3000 N/M, about 4000 N/M or about 5000 N/M or any value therebetween. In some particular embodiments, K is about 3000 N/M.

Also, other resilient components and/or translatable member configurations can be used can be used with or instead of the coil spring and with or without the rod(s). For example, one or more leaf springs, (stacked) dome washers, one or more O-rings or washers, Belleville springs, Clover-Dome spring washers (see, e.g., U.S. Pat. No. 6,705,813), or any other type of flexible elastic member including, for example a solid resiliently deformable elastic (polymeric) member (polyurethane or other suitable material). Combinations of different types of elastic or resilient members and/or more than one of the same type may also be used.

As shown in FIG. 1, the adaptor 30 can include translatable members 35 that can face each other across an open medial portion 30p of the adapter, e.g., on opposing sides of the probe 20, and can, in concert, linearly retract, compress or deform with a defined stiffness to allow the sensor to generate the applied force measurement. As will be discussed further below, the translatable member(s) 35 can have an adjustable stiffness so that the linear movement for a particular applied force or set of forces varies according to target tissue or patient (e.g., pediatric versus adult or athlete and the like).

In some embodiments, where resilient members 37 are used, the resilient (elastically deformable) members 37 can be configured to have a defined k-factor (spring constant) and/or stiffness. The members 37 can be selected for use with the adaptor 30 based on different target tissues or patients. Where gas cylinder dampers (miniature) are used, the actuation stroke associated with the cylinder/gas can be adjusted for different tissue/patients.

Figure 3A:
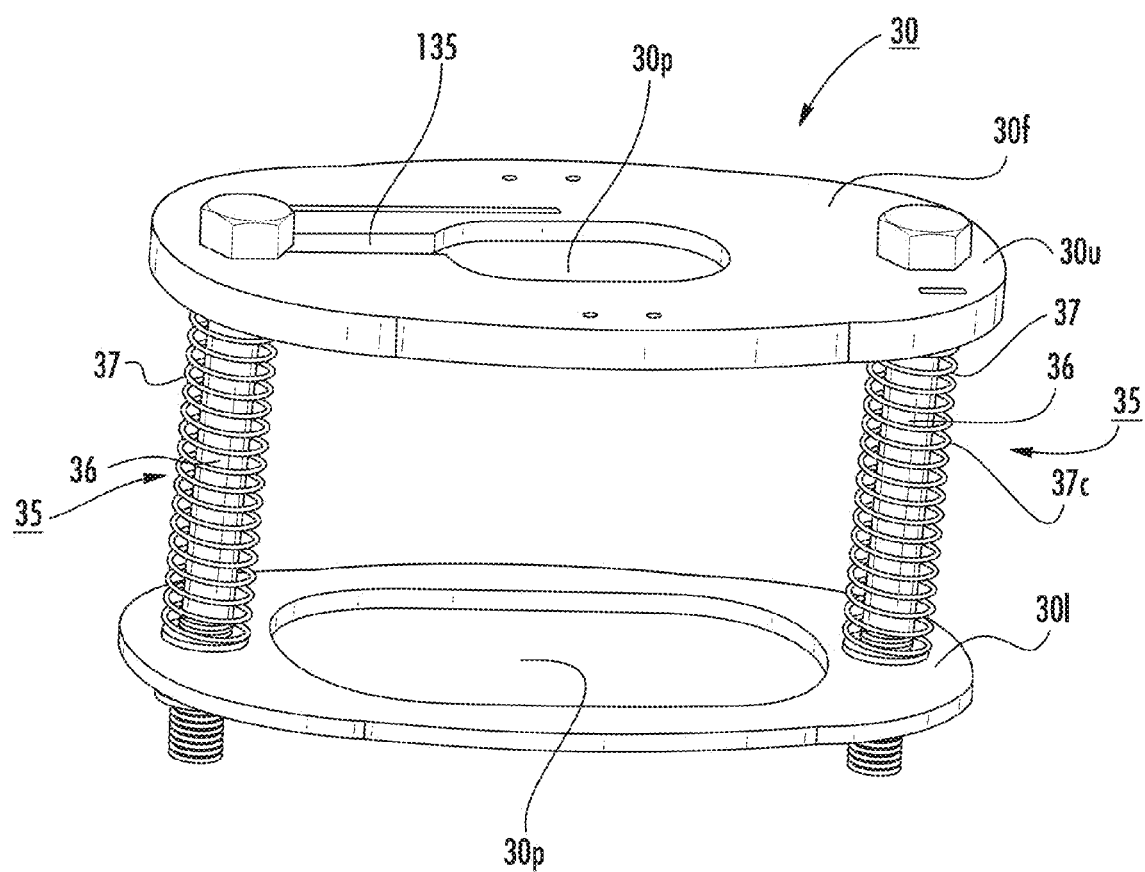
FIG. 3A is a front perspective view of an assembled adaptor body according to embodiments of the present invention.
Figure 3B:
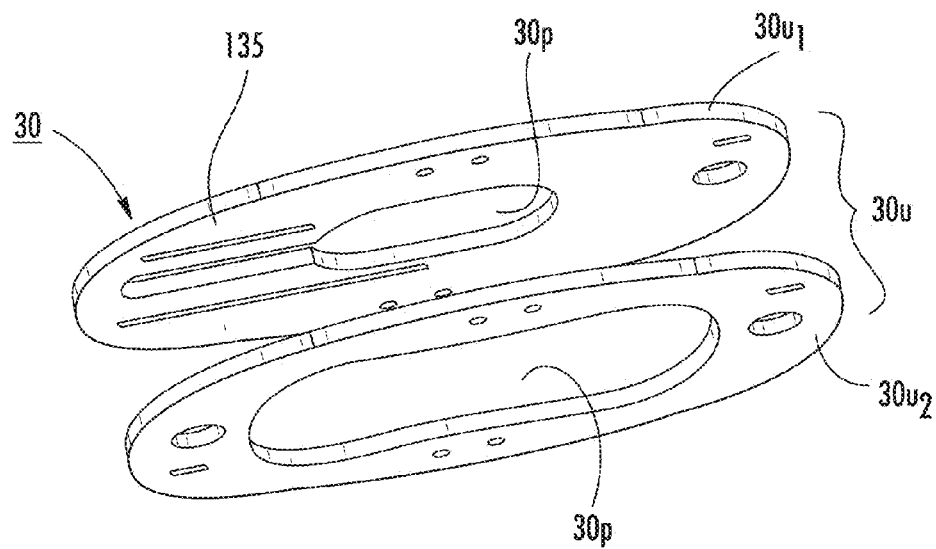
FIG. 3B is a partially exploded view of the adaptor body shown in FIG. 3A.
Figure 3B:
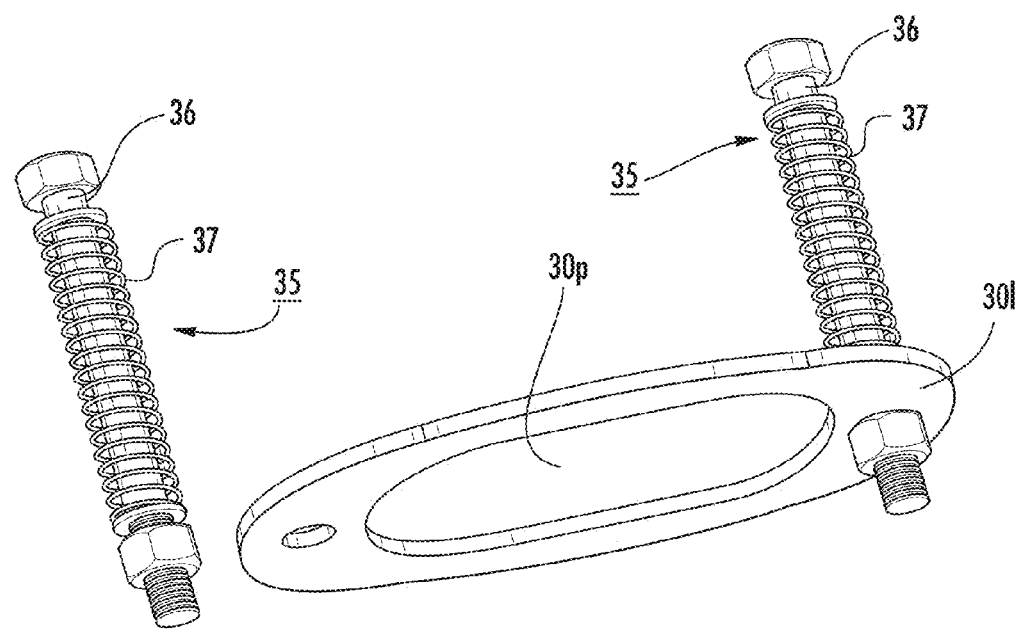

In some embodiments, the adaptor 30 can be a "universal" adaptor meaning that it can be assembled to different probes 20 from the same or even different manufacturers. As shown in FIGS. 1, 3A-3D, the adaptor 30 can have a frame 30f with an open frame body configuration with upper and lower cooperating horizontally oriented frame members 30u, 30l that trap two laterally spaced apart rods 36 attached to the frame members inside two resilient members 37. An open slot 135 in the upper frame 30u cooperates with a collar 33 (FIG. 1) or other mounting member that can be provided in different sizes to provide the probe to adaptor interface adjustability to allow for assembly to different probe bodies using a common primary adaptor body such as a frame body. In other embodiments, the adaptor 30 can be configured to attach to a specific probe configuration. In this embodiment, the adaptor 30 has a frame 30f with an open frame body that allows visual access to the probe 20. FIG. 3B illustrates that the upper frame member 30u can include two closely spaced cooperating members that hold the probe proximal or upper end. Open center spaces 30p can be aligned with the top frame member having a smaller opening relative to the underlying upper frame member $30u_1$, $30u_2$, respectively. FIGS. 3A and 3B are shown in a partial assembly configuration without the sensors and it is also noted that the lower threaded portions of the rods typically do not extend outside the lower frame surface (or at least do not contact the patient) for patient comfort.

Figure 3C:
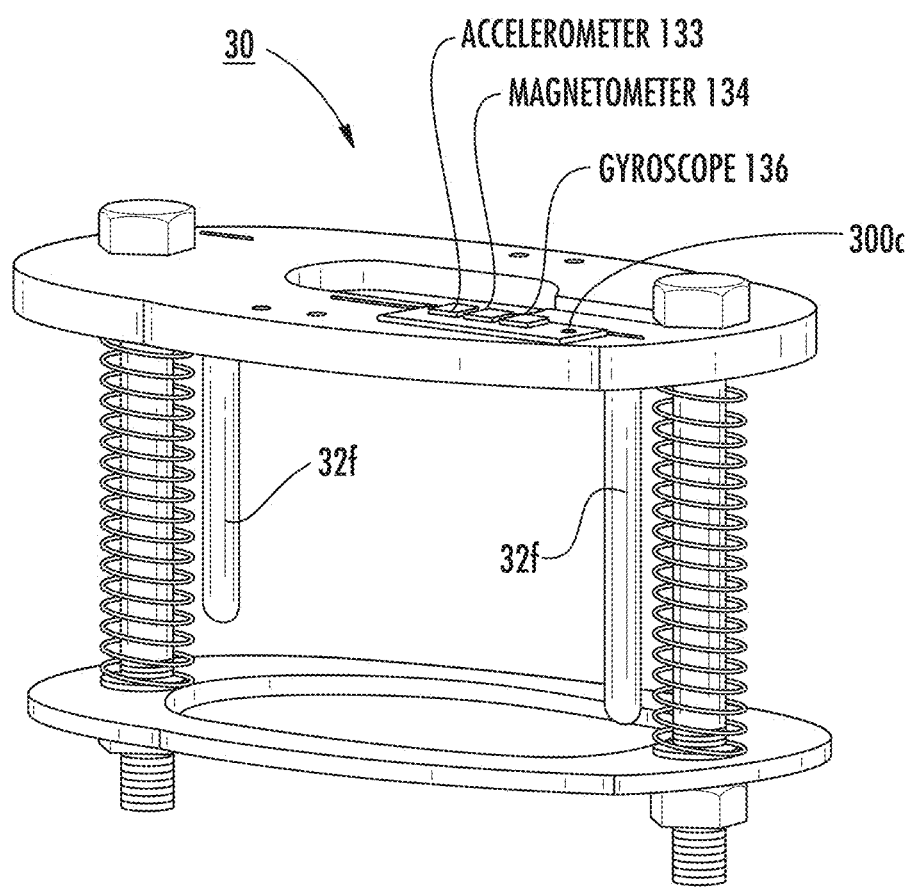
FIG. 3C is a front perspective view of the adaptor body shown in FIG. 3A illustrating sensors that can be included according to embodiments of the present invention.
Figure 3D:
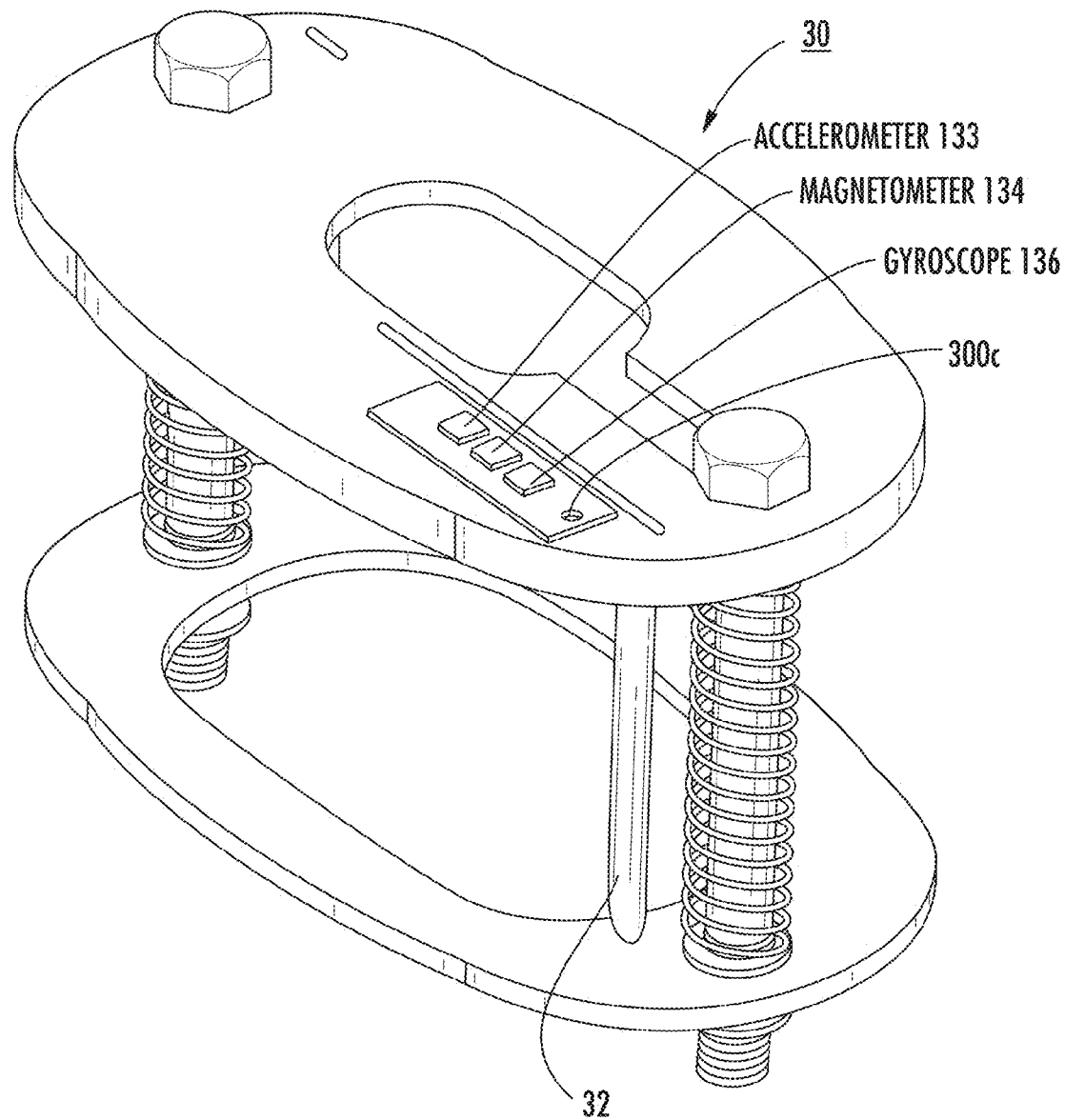
FIG. 3D is a top perspective view of the adaptor body shown in FIG. 3C.
Figure 3E:
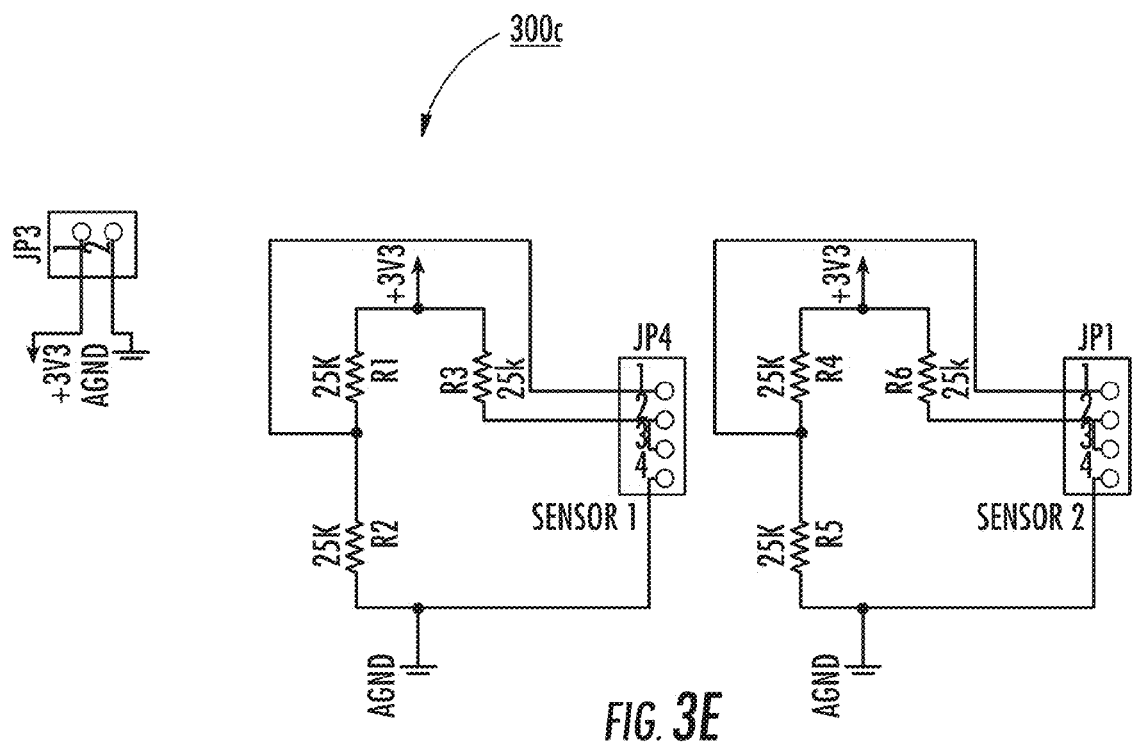
FIG. 3E is a schematic circuit diagram of the sensor circuit shown in FIG. 3D according to embodiments of the present invention.

FIGS. 3C and 3D illustrate the adaptor 30 with two flex sensors 32f. FIGS. 3C and 3D also illustrate a circuit board 300c (which can be a rigid or substantially rigid printed circuit board or a flex circuit) with three sensors thereon, including an accelerometer 133, a magnetometer 134 and a gyroscope 136. FIG. 3E illustrates an exemplary circuit schematic of the circuit 300c.

The adaptor 30 may also include an angulation and accelerometer sensor. The adaptor 30 can be battery powered, may be AC powered into a power source or may be powered by connecting to a port of a portable device, e.g., smart phone or notebook.

FIG. 5A illustrates that the adaptor 30 can have a body 30b that can be more form-fitting, e.g., having a shape substantially similar to the body of the probe 20 and may have upstanding walls 30w that encase a respective probe 20 while leaving the distal end 30d open and free to contact a patient. The adaptor 30 can have a substantially closed shell or case body with matably attachable front and back components 30c as shown in FIG. 5A. The adaptor 30 may also have a body that substantially encloses the probe body but may have an external shape that is different than the probe 20.

Figure 5B:
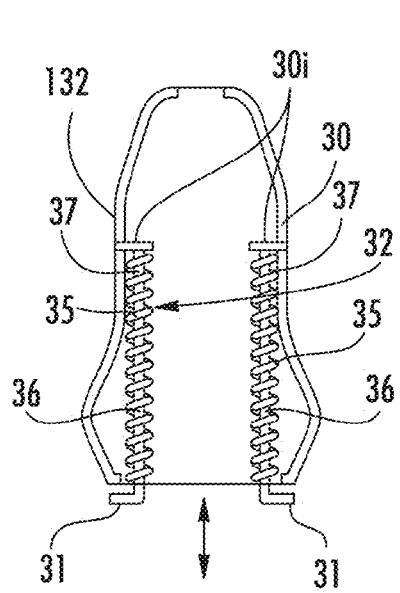
FIG. 5B is a front schematic view of the adaptor body shown in FIG. 5A with exemplary force sensor and translatable members according to embodiments of the present invention.

FIG. 5B illustrates that the internal wall 30i of the shell or case 30c can hold the translatable member 35 of the force sensor 32, shown as comprising resilient members 37 held in place with rods 36. The rods 36 can slidably move up and down relative to the upper ledge, e.g., through a slot or hole. The rods 36 can have feet that can form part of a patient contacting surface 31 used to define linear movement for measuring applied force.

FIGS. 1, 5B, 5C, 5D and 5E also illustrate that the adaptor 30 can have a patient contacting surface 31 that abuts against skin of the patient and translates in an opposing direction away from the compression direction of the probe 20 as the probe 20 pushes inward/down to compress target tissue being imaged. The patient contacting surface 31 can be defined by a substantially rigid portion of the probe body.

The patient contacting surface 31 can be annular and surround the probe 20 as shown in FIG. 1. FIGS. 5A and 5B illustrate that the surface 31 is not required to surround the probe 20. This surface 31 may be discontinuous about the probe perimeter.

Figure 5C:
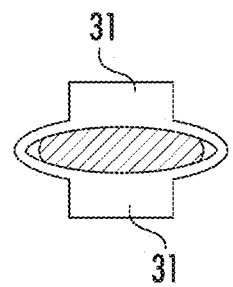
FIGS. 5C-5E are end views of alternate configurations of adaptor body cases according to embodiments of the present invention.
Figure 5D:
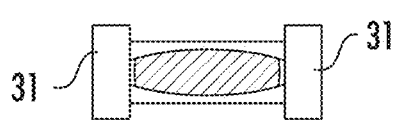

FIGS. 5C and 5D illustrate different exemplary embodiments of the patient-contacting surface 31 of the adaptor 30 for the force sensor 32. FIG. 5C illustrates the patient contacting surfaces 31 on the opposing long sides of the adaptor 30 while FIG. 5D illustrates the patient contacting surfaces 31 on the adaptor short sides. The surfaces 31 can also reside on all sides. The term "sides" does not require the perimeter to have a rectangular shape as other geometric shapes may be used.

Figure 5E:
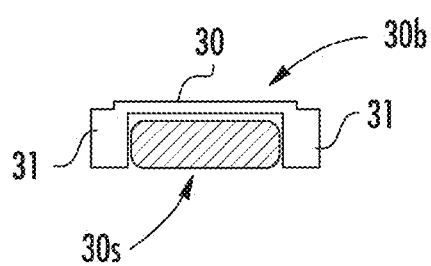

FIG. 5E illustrates that the adaptor body 30b can partially enclose the probe body 20 to leave an open long space 30s on one side for ease of assembly. A cover plate may be attached to the open space 30s of the body 30b or this space 30s can remain open during use. In other embodiments, the adaptor body 30b only includes one of the shell or case components 30c shown in FIG. 5A, leaving the probe open on one side.

As shown in FIGS. 1, 5B, 5C, 5D and 5E, the adaptor 30 is configured to define an open bottom that allows the probe 20 to directly contact the patient's skin.

The surface 31 can be substantially flat and may have ridges, ribs, embossment features or grip regions. Typically, the surface 31 has a symmetric shape and is sufficiently large to provide adequate support for allowing the surface to push in an opposing direction from the probe 20 for a transducer to generate the applied force measurement. The surface 31 can have a width that is between about 0.1 inches to about 0.5 inches in some embodiments. The surface 31 can have a constant width about its perimeter or the width may vary over its perimeter.

As noted above, different adaptors 30 can be provided with predefined/known different stiffness for the defined linear movement to force relationship. In some embodiments, translatable members 35 and/or the members 37 themselves can be interchanged on a respective adaptor 30 to use those from a kit of defined resilient members.

FIGS. 1 and 3A illustrate different coil springs 37c (one has a different stiffness than the other) that may be used with the same adaptor 30. Different rated members 35 can be color coded or marked by rating for a user's ease in selecting for concurrent use on a respective device 30, for ease of identification. The translatable members 35, e.g., springs or other resilient members 37, can include electronically readable media, e.g., barcodes, linear or 2-D (e.g., QR) barcodes or that can be read by the ultrasound system 50 (FIG. 4), and/or a portable computer (e.g., electronic notebook or smart phone), or an electronic reader onboard or in communication with the adaptor 30 to confirm or identify a part number, type or rating of member 35 that is on-board the device 30 and to optionally confirm that each translatable member station/position has a the same stiffness-rated resilient member (or activation can be locked out, an audible or visual alert can be generated or an error may be displayed on a display). Alternately, a user can enter the type and/or stiffness rating of member 35 for use.

Figure 4:
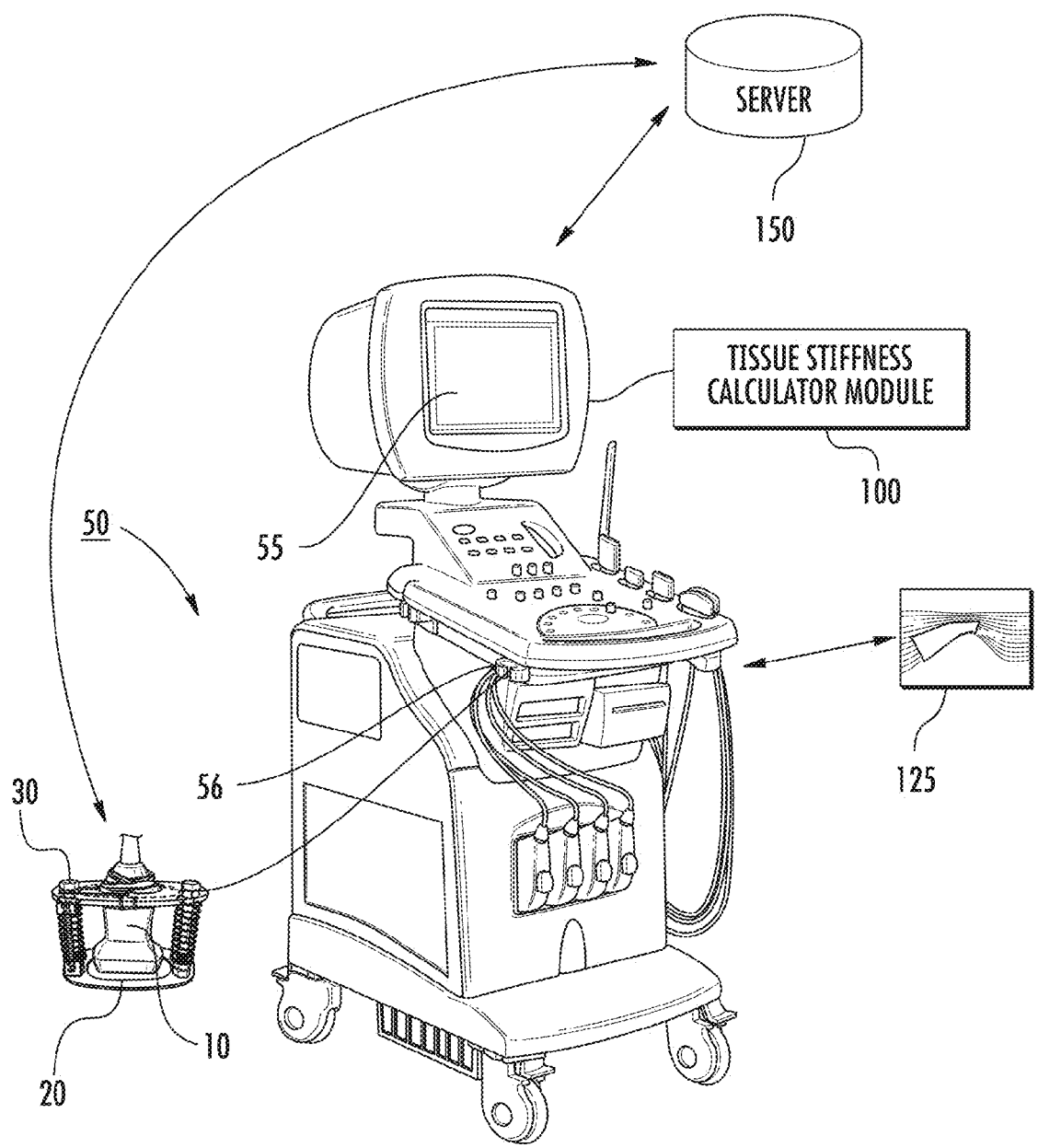
FIG. 4 is a schematic illustration of an ultrasound elastography system according to embodiments of the present invention.

FIG. 4 illustrates an exemplary ultrasound system 50 that is in communication with the probe 20 and includes or is in communication with a tissue stiffness calculation module 100 that uses data from the applied-force measurement adaptor 30 and compression measurements from an ultrasound images taken of compressed tissue. The compressed tissue image is synchronized with a corresponding applied force measurement so that the force used to cause the change in tissue thickness in the compressed tissue is defined. The adaptor 30 can connect to an input port 56 on the ultrasound system (e.g., a USB or other defined port). In some embodiments the adaptor 30 can connect to a separate device 125 such as a remote device instead or in addition to the ultrasound device 50.

The module 100 can reside partially or totally on-board the ultrasound system 50 (e.g., in the computer and/or processor thereof) or can reside partially or totally remotely in one or more remote processors. The module 100 can reside on the separate device 125 which can be a portable electronic device such as a laptop, smart phone (e.g., IPHONE™), notebook or other pervasive computing device that wirelessly or in a wired manner communicates with the adaptor 30 and/or ultrasound system 50 for access to the ultrasound compressed image data (e.g., an ultrasound image module) and the applied force data from the adaptor 30. The module 100 can partially or totally reside in a server such as in a PICTURE ARCHIVING AND COMMUNICATION SYSTEM ("PACS") system. The module 100 can be configured to transmit images and overlays to a server such as a PACS server and may record or match force measurements in image metadata. PACS is a system that receives images from imaging modalities, stores the data in archives, and distributes the data to clinicians for viewing (and can refer to sub portions of these systems).

The term "module" is used interchangeably with "circuit" and refers to an entirely software embodiment or an embodiment combining software and hardware. The module or modules can reside in one or more signal processors that include or communicate with electronic memory. The processor(s) can be any commercially available or custom microprocessor. The memory is representative of the overall hierarchy of memory devices containing the software and data used to implement the functionality of the data processing system. The memory can include, but is not limited to, the following types of devices: cache, ROM, PROM, EPROM, EEPROM, flash memory, SRAM, and DRAM.

As noted above, the circuit or module 100 can synchronize a force measurement from the adaptor 30 with the corresponding compressed ultrasound image. The module 100 can reside on the ultrasound system 50, in the separate device 125 which can be a mobile device (such as in an APP on that device), on-board the adaptor 30, in a PACS or hospital database or one or more remote servers 150. The one or more servers 150 can be provided using cloud computing which includes the provision of computational resources on demand via a computer network. The resources can be embodied as various infrastructure services (e.g. computer, storage, etc.) as well as applications, databases, file services, email, etc. In the traditional model of computing, both data and software are typically fully contained on the user's computer; in cloud computing, the user's computer may contain little software or data (perhaps an operating system and/or web browser), and may serve as little more than a display terminal for processes occurring on a network of external computers. A cloud computing service (or an aggregation of multiple cloud resources) may be generally referred to as the "Cloud". Cloud storage may include a model of networked computer data storage where data is stored on multiple virtual servers, rather than being hosted on one or more dedicated servers. Data transfer can be encrypted and can be done via the Internet using any appropriate firewalls to comply with industry or regulatory standards such as HIPAA. The term "HIPAA" refers to the United States laws defined by the Health Insurance Portability and Accountability Act. The patient data can include an accession number or identifier, gender, age and force measurement data as meta data for the ultrasound images.

Figure 6B:
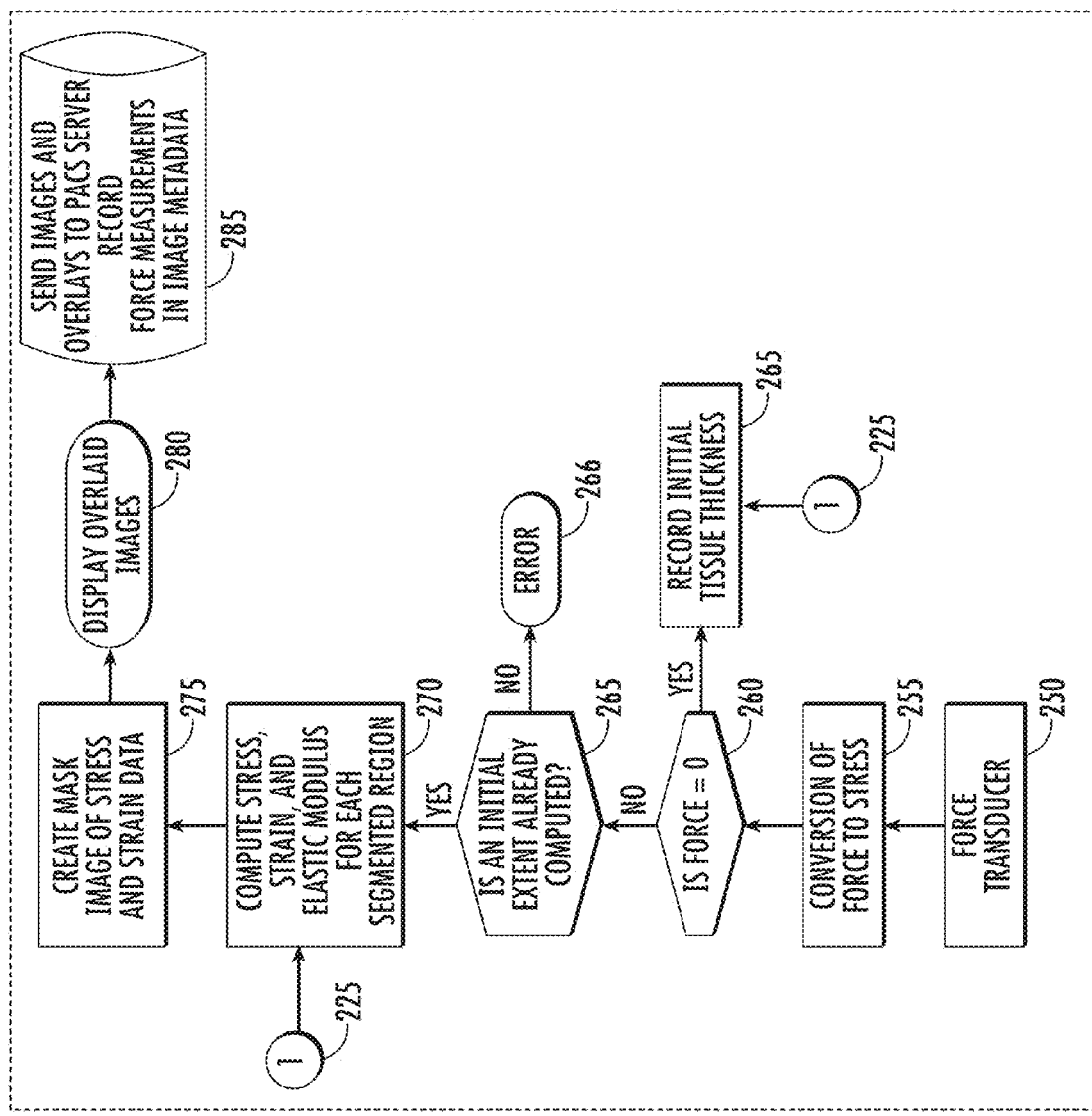
FIGS. 6A and 6B are flow charts of exemplary operations that can be used to carry out embodiments of the present invention.
Figure 6A:
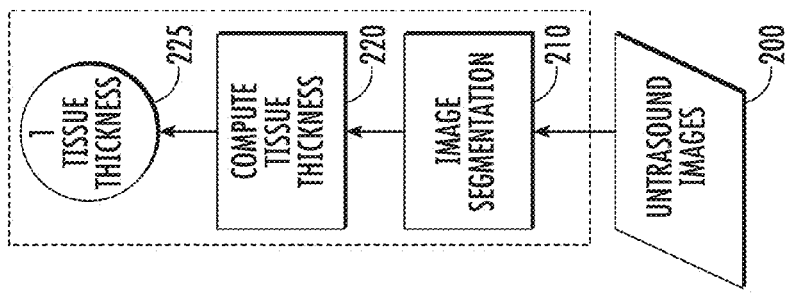

FIG. 6A is a flow chart of exemplary preliminary operations that can be used to calculate tissue thickness before compression of tissue (e.g., when the applied force is "0") which may be carried out prior to activation of the adaptor 30. One or more ultrasound images can be obtained (block 200) and electronically segmented (block 210). Tissue thickness can be computed (block 220) and provided as a parameter of "tissue thickness 1" (block 225). The adaptor 30 with the force transducer can be activated (block 250). The force measurement is used to calculate stress (block 255) based on a known value of surface area of the probe in use. If the force is "0", the initial tissue thickness can be defined for this "at rest" or pre-compression evaluation to define an initial tissue thickness (block 265). This thickness can be defined as the original length ($l_o$). Where the steps of FIG. 6A have also been performed, the two values of initial thickness ($l_0$) may be compared the value from block 225 and the value from block 265. If there is a difference, an alert may be generated or if within a defined tolerance an average measurement can be used. Steps 250-260 may be omitted where steps 200-225 were previously carried out. In any event, the system may generate an error alert if the initial extent has not been computed (block 266). Of course, the initial extent can also be calculated after the compressed extent is calculated. As shown, stress, strain, and Elastic Modulus are calculated/computed for each segmented region of interest (for moving joints, potentially at different angles) (block 270). A mask or color-coded overlay image or color-coded image itself of stress and strain data (e.g., Modulus) can be created (block 275). The overlays of the stress/strain data can be displayed (block 280). The ultrasound images and associated overlays can be sent to a server (such as a PACS server) and force measurements can be recoded/appended to image metadata (block 285).

Figure 7:
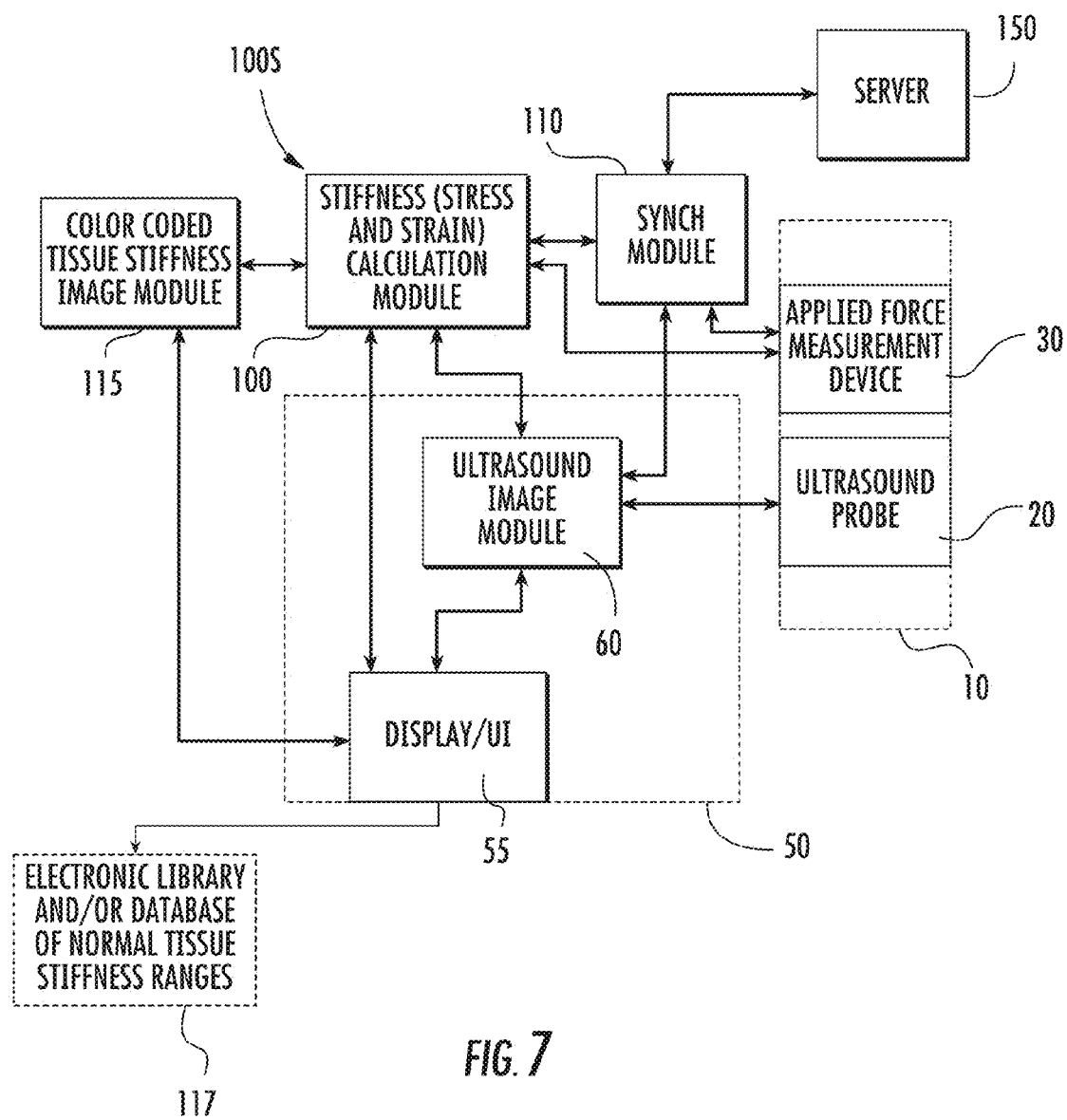
FIG. 7 is a block diagram of a system according to embodiments of the present invention.

FIG. 7 is a schematic illustration of a system 100s with a stiffness (stress/strain) calculation module 100 that is in communication with a synchronization module 110, a color-coded tissue stiffness image module 115, an ultrasound image module 60 and a display 55. As shown, the display 55 can be on-board the ultrasound system 50 but may also be associated with a different device or both the on-board display and a different display. The system 100s can communicate with a PACS or other server 150.

The system 100s may include or be in communication with an electronic library or database 117 of population norms or standards/ranges that allow a clinician to compare normal or abnormal measurements of tissue stiffness for different defined tissues and the population norms/standards can be further segmented or grouped by/age, gender and ethnicity. Embodiments of the invention can generate an audio or visual alert when abnormal measurements for a target tissue are calculated and/or when measurements taken over time indicate an increase in the risk of injury or disease progression.

Because of the degenerative nature of rotator cuff disease, early diagnosis may be key to preventing disease progression. A quantitative assessment of tissue material properties may be able to be used as a predictive screening test or be used to properly stage patients for treatment, which may be particularly suitable for rotator cuff disease, which has a high incidence, with a high societal cost. This incidence is correlated with age, and as the population ages, the cost of this disease will only increase. Thus, the use of ultrasound elastography may predict the occurrence of rotator cuff disease, thus allowing for early diagnosis treatment. Through this early diagnosis, there may be a net reduction in the necessary treatment, and thus total cost of this common and debilitating disease.

Figure 8:
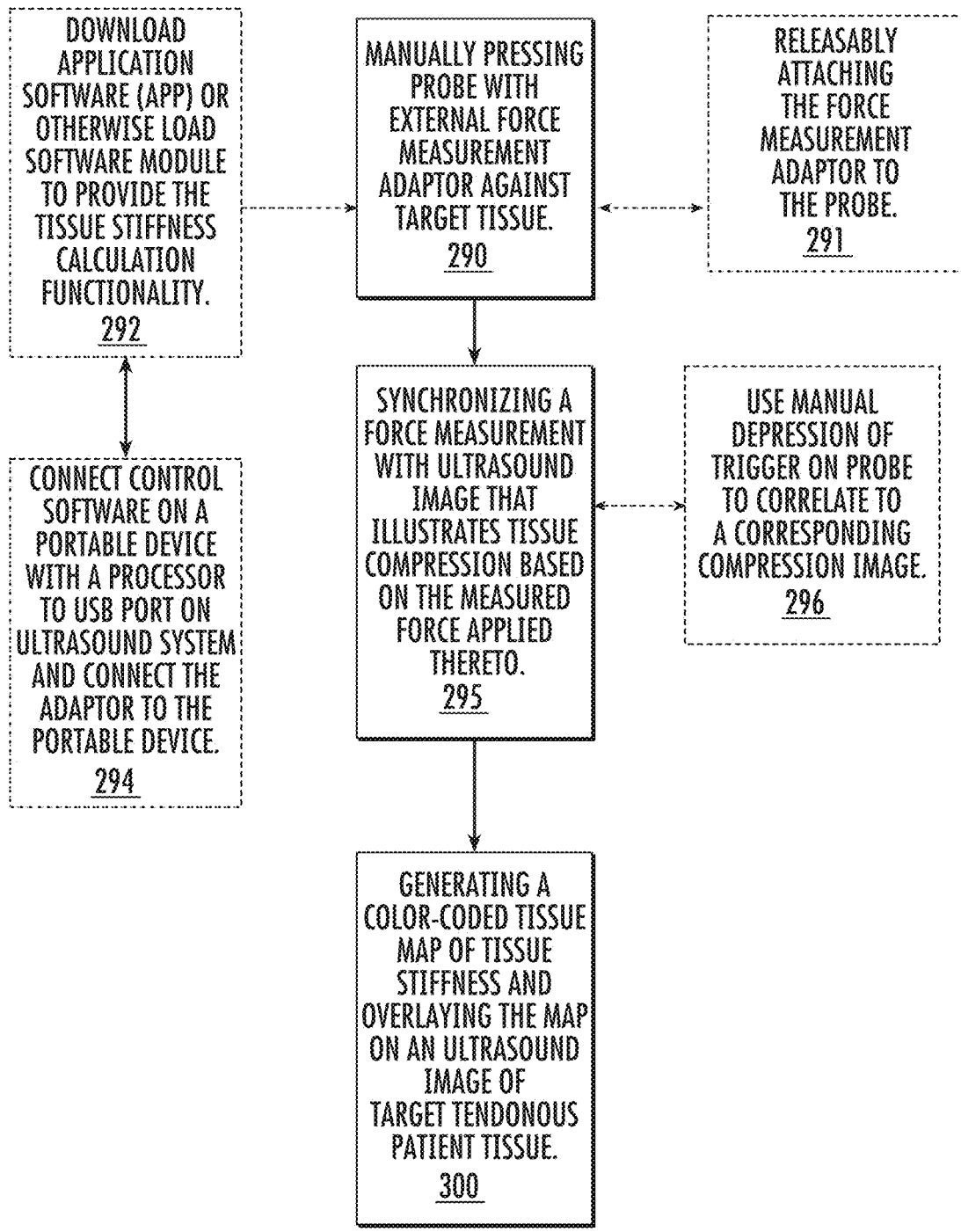
FIG. 8 is a flow chart of exemplary operation that can be used to carry out embodiments of the present invention.

FIG. 8 is a flow chart of operations that can be used to carry out embodiments of the present invention. The ultrasound probe is manually pressed against skin to compress target tissue (block 290). A force measurement is synchronized with the ultrasound image obtained using the associated force that provides the tissue compression in that image (block 295). A color-coded tissue map can be generated and overlayed or applied to ultrasound image data of tendonous patient tissue (block 300).

The adaptor can be releasably attached to the probe (block 291). A software application (APP) can be downloaded or the software module can otherwise be loaded onto one or more processors to provide a tissue stiffness calculation functionality (block 292). Control software on a portable device with a processor can be connected to a USB port on the ultrasound system and/or the adaptor can be connected to the portable device and/or USB port on the ultrasound system (block 294).

A manual depression of a trigger on or associated with the ultrasound probe used to obtain the image can be used to synchronize the force measurement to correlate to the appropriate image and may include a time stamp (block 296).

The adaptor 30 can be portable and may universally fit to existing ultrasound probes of commercially available systems. The adaptor 30 can include an onboard display or transmit data to the ultrasound display so that the applied force value of an associated image can be substantially continually displayed (and may be displayed with off and on GUI user selection). The systems can provide synchronization between force, imaging, and positional data of the patient. Using force and image data, the local tissue elasticity (or stiffness) can be computed. Image overlays can be made to show local elasticity. Based on the elasticity data, a database of patient data for future diagnostic evaluations/tools can be generated. The tissue elasticity measurements can objectively assess tissue and quality of images.

The devices and systems can be used to evaluate or screen athletes, particularly young (college age and younger) athletes. Due to repeated motion and traumatic injury, athletes may have tears at younger ages. The device is non-invasive and poses no patient risk and can act as screening test before clinical injury is reached. Embodiments of the invention can provide a technology to improve tendon pathology diagnosis, reduce unnecessary and costly treatments, and unnecessary surgical intervention.

Figure 9:
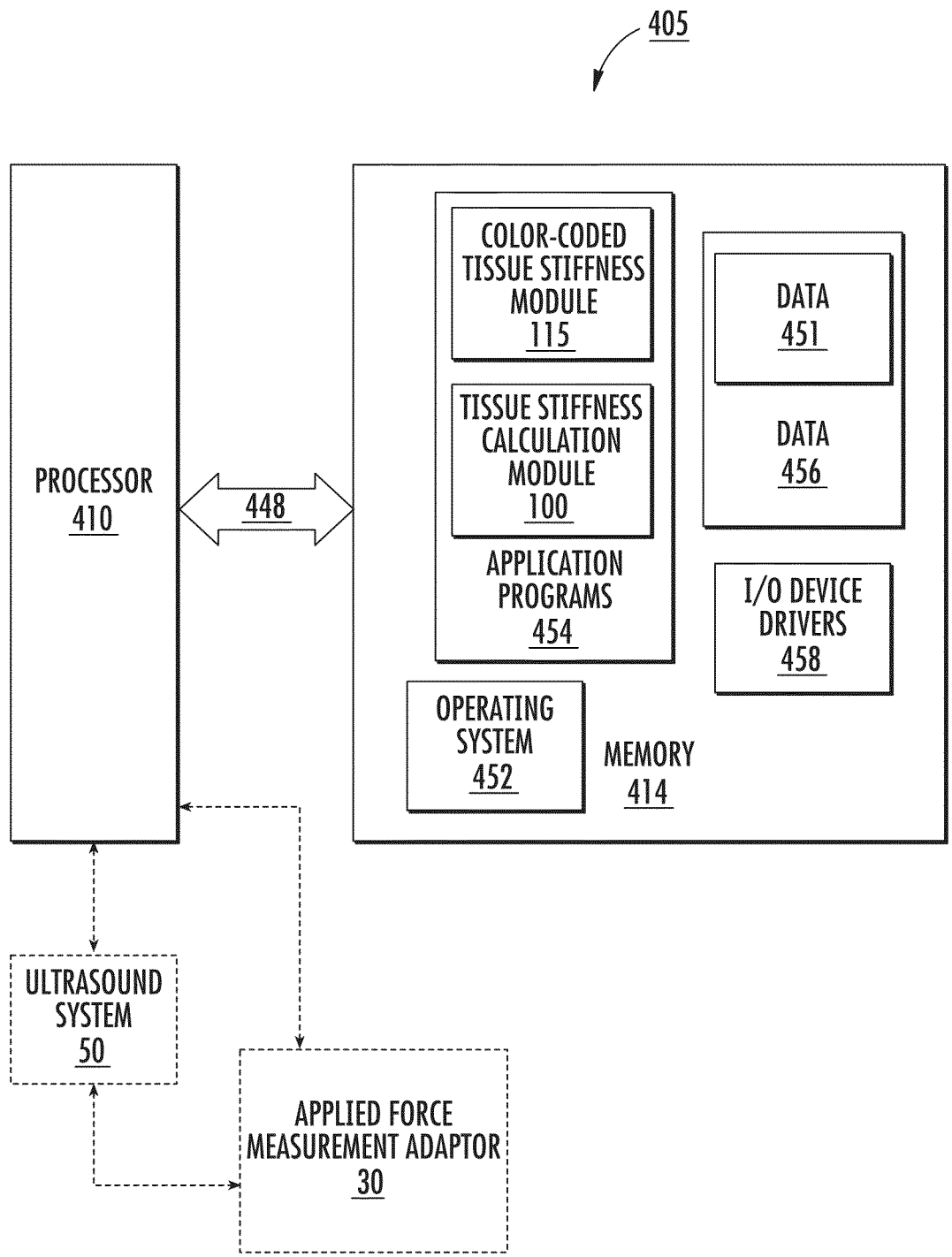
FIG. 9 is a block diagram of a data processing system according to embodiments of the present invention.

FIG. 9 is a block diagram of exemplary embodiments of data processing systems 405 that illustrates modules, circuits, systems, methods, and computer program products in accordance with embodiments of the present invention. The processor 410 (which can optionally be part of the ultrasound system 50) communicates with the memory 414 via an address/data bus 448. The processor 410 can be any commercially available or custom microprocessor. The memory 414 is representative of the overall hierarchy of memory devices containing the software and data used to implement the functionality of the data processing system 405. The memory 414 can include, but is not limited to, the following types of devices: cache, ROM, PROM, EPROM, EEPROM, flash memory, SRAM, and DRAM.

As shown in FIG. 9, the memory 414 may include several categories of software and data used in the data processing system 405: the operating system 452; the application programs 454; the input/output (I/O) device drivers 458; the tissue stiffness calculation module 100; the color-coded. tissue stiffness module 115 and the data 456. The data 456 may include a table of operational parameters, including force, area, strain, stress and/or Elasticity Modulus. As will be appreciated by those of skill in the art, the operating system 452 may be any operating system suitable for use with a data processing system, such as OS/2, AIX, OS/390 or System390 from International Business Machines Corporation, Armonk, N.Y., Windows CE, Windows NT, Windows95, Windows98 or Windows2000, Windows VISTA from Microsoft Corporation, Redmond, Wash., Unix or Linux or FreeBSD, Palm OS from Palm, Inc., Mac OS from Apple Computer, LabView, or proprietary operating systems. The I/O device drivers 458 typically include software routines accessed through the operating system 452 by the application programs 454 to communicate with devices such as I/O data port(s), data 451, data storage 456 and certain memory 414 components and/or the dispensing system 420.

The application programs 454 are illustrative of the programs that implement the various features of the data processing system 405 and preferably include at least one application which supports operations according to embodiments of the present invention. Finally, the data 456 represents the static and dynamic data used by the application programs 454, the operating system 452, the I/O device drivers 458, and other software programs that may reside in the memory 414.

While the present invention is illustrated, for example, with reference to the modules 100, 115 being application programs in FIG. 9, as will be appreciated by those of skill in the art, other configurations may also be utilized while still benefiting from the teachings of the present invention. For example, the module 100 and/or 115 may also or alternately be incorporated into the operating system 452, the I/O device drivers 458 or other such logical division of the data processing system 405. Thus, the present invention should not be construed as limited to the configuration of FIG. 9, which is intended to encompass any configuration capable of carrying out the operations described herein.

The I/O data port can be used to transfer information between the data processing system 405 and a remote processor or another computer system or a network (e.g., an intranet and/or the Internet and/or PACS) or to other devices controlled by or in communication with the processor. These components may be conventional components such as those used in many conventional data processing systems which may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configuration of FIG. 9 but is intended to encompass any configuration capable of carrying out the operations described herein.

The flowcharts, schematic illustrations and block diagrams of certain of the figures herein illustrate the architecture, functionality, and operation of possible implementations according to the present invention. In this regard, each block in the flow charts, schematic illustrations or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

Figure 10:
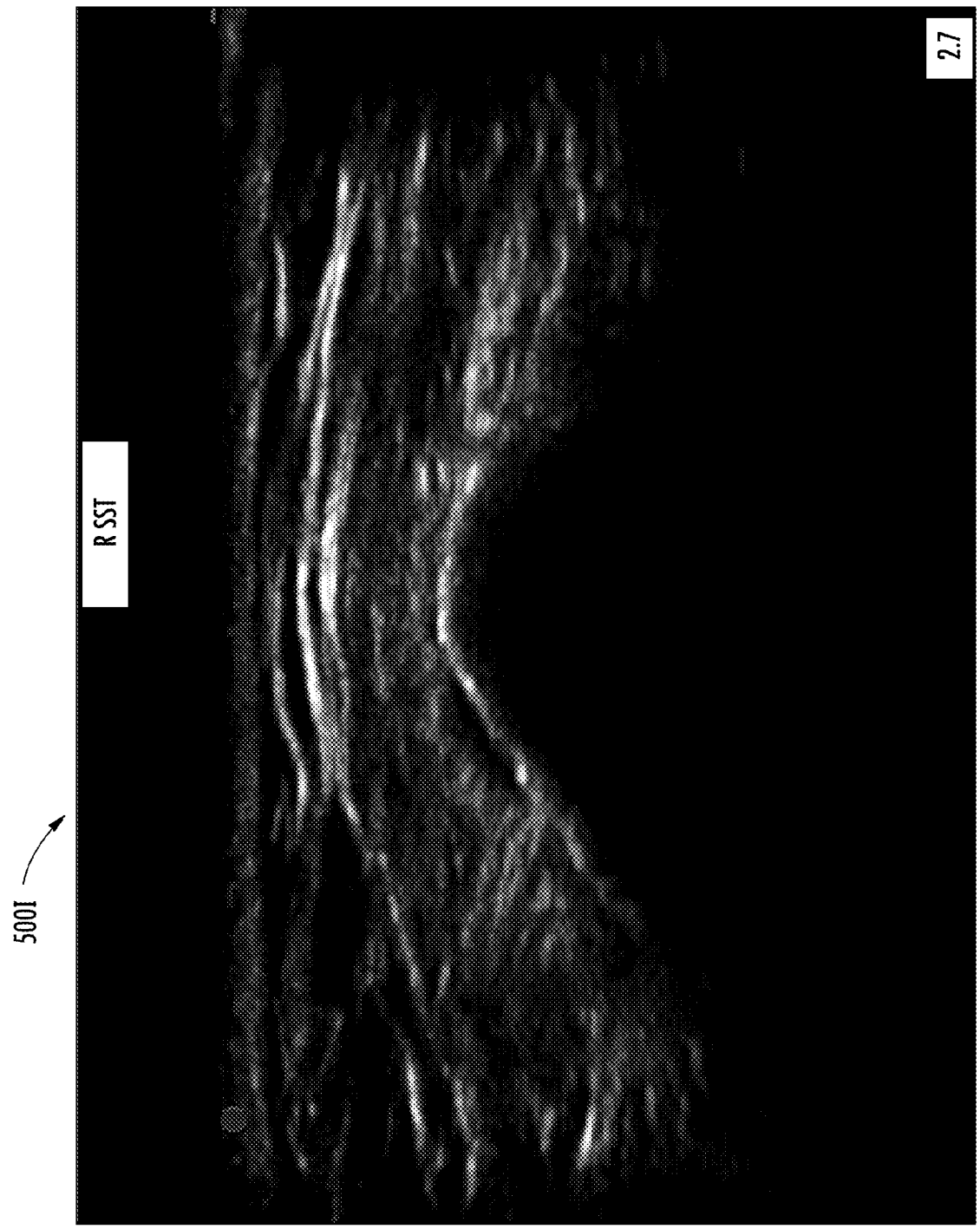
FIG. 10 is an ultrasound image of tissue associated with a rotator cuff of a patient.
Figure 11:
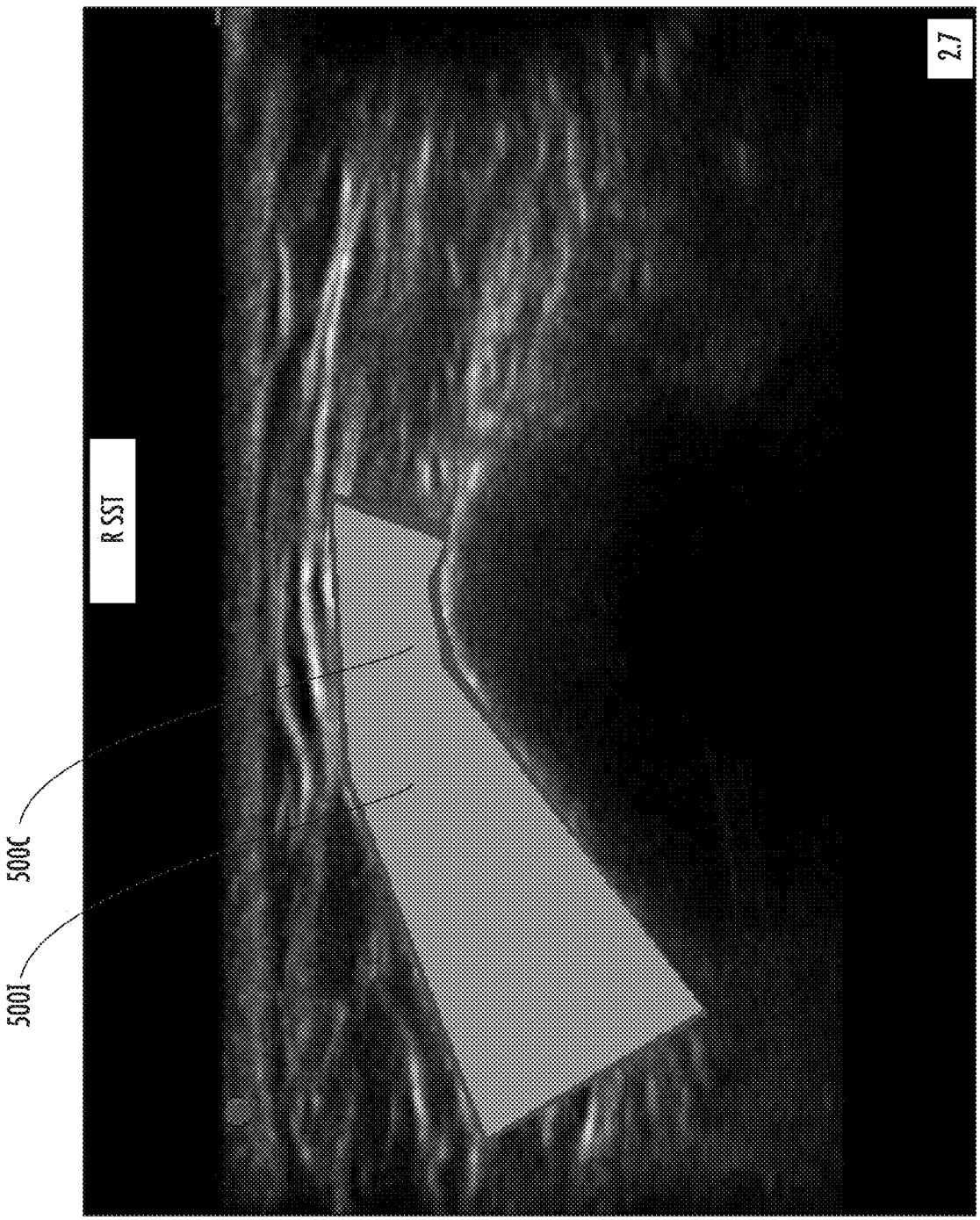
FIG. 11 shows the ultrasound image of FIG. 10 with a prophetic color coded overlay of tissue elasticity/stiffness that associates color with objective measured/calculated elasticity values according to embodiments of the present invention.

FIG. 10 illustrates an ultrasound image of compressed target tissue 500I and FIG. 11 illustrates this same image 500I with a prophetic color-coded overlay of tissue elasticity (stiffness) 500c of target tissue within the image.

EXAMPLES

Figure 13:
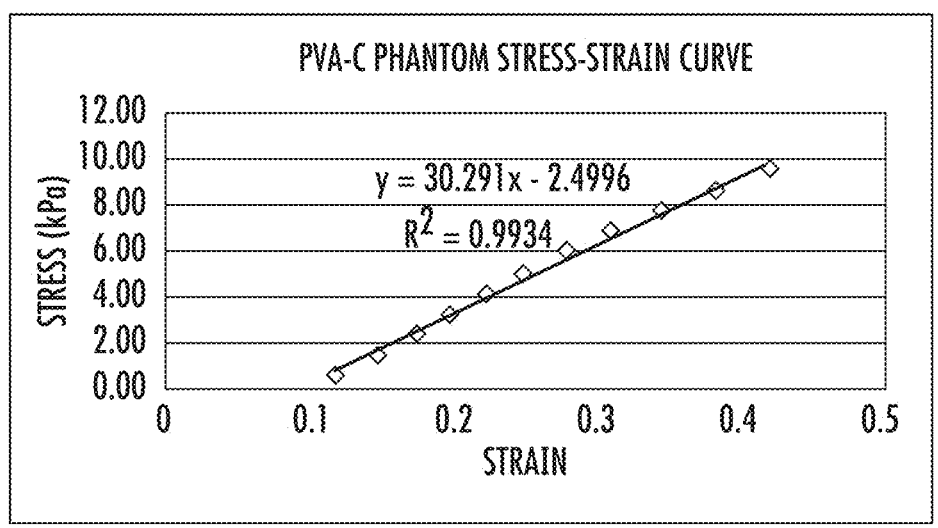
FIG. 13 is a graph of stress (kPa) versus strain that was used to determine the Young's modulus for PVA-C phantom.

To demonstrate proof of concept a polyvinyl alcohol cryogel (PVA-C) phantom was created and analyzed using the device shown in FIG. 1. During the validation study, the material was subjected to stress using an ultrasound transducer and strain was assessed from the ultrasound images using a manual measurement. FIG. 13 shows the computed stress-strain curve on one gel sample. The measured stress-strain curve was monotonic linear ($R^2 > 0.99$), with an inherent dampening offset of 2.4996 kPa. The Young's modulus in this test was 30.291 kPa, which is similar to values for this material that are reported in the literature. See, e.g., Fromageau et al., "Estimation of polyvinyl alcohol cryogel mechanical properties with four ultrasound elastography methods and comparison with gold standard testings," *Ultrasonics, Ferroelectrics and Frequency Control, IEEE Transactions on*, vol. 54, no. 3, pp. 498-509, March 2007 and Fromageau et al., "Characterization of PVA cryogel for intravascular ultrasound elasticity imaging," *Ultrasonics, Ferroelectrics and Frequency Control, IEEE Transactions on*, vol. 50, no. 10, pp. 1318-1324, October 2003.

Figure 12:
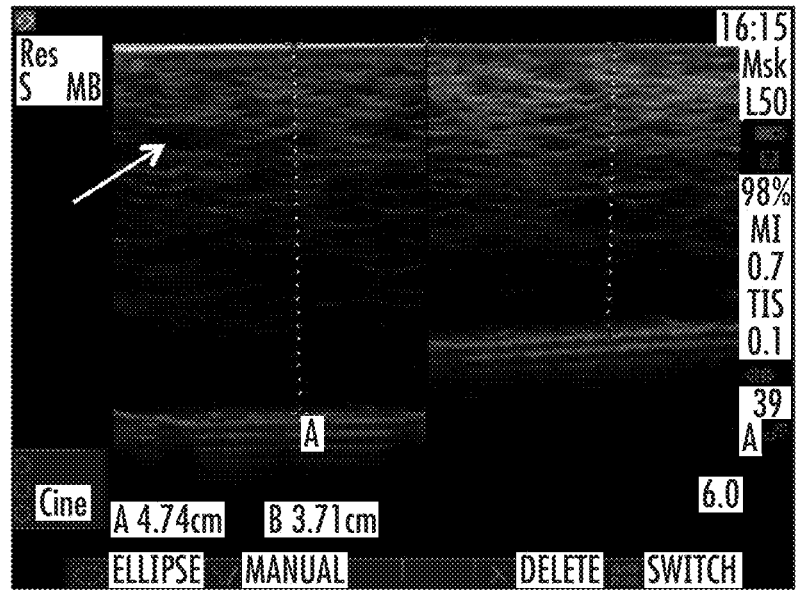
FIG. 12 shows side by side ultrasound images of Ecoflex® 00-30, with the window on the right associated with compressed material, and with the window on the left showing an arrow indicating bubbles increasing attenuation of the ultrasound signal.

Further material testing was conducted using Ecoflex® 00-30, a platinum-catalyzed silicone. Using a Bose Electro-Force 3200, various compression tests were performed and the results indicated a Young's modulus of 53.02 kPa at approximately a 10 percent strain. Testing was conducted as in the previous PVA-C study. However there was increased, attenuation of the ultrasound signal as a result of large amounts of air bubbles cast within the Ecoflex® 00-30. This resulted in an inaccurate ultrasound image and thus an invalid measurement of the material deformation (FIG. 12). To eliminate the signal attenuation, the deformation of the Ecoflex® 00-30 was measured by hand using a standard ruler and the Young's modulus was determined to be 57.39 kPa at approximately a 9 percent strain. The discrepancy in the Young's modulus value calculated using the Bose ElectroForce 3200 and the determined value is likely due to the limitations of the deformation measurement not on the reliability or accuracy of the force measurement as the stress values were within 0.1 kPa of one another.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

That which is claimed:

1. An adaptor for an ultrasound probe, comprising:
   an adaptor body releasably attachable to an outer portion of an ultrasound probe, the adaptor comprising at least one force sensor configured to obtain a force measurement of force applied to target tissue by a respective ultrasound probe during an ultrasound evaluation of a patient, wherein the adaptor body has cooperating upper and lower members that releasably hold the ultrasound probe, the lower member having a lower end with an open portion that allows a distal end of the ultrasound probe to extend therethrough, wherein the lower member of the adaptor body has at least one distalmost segment that defines a skin contacting portion and, in use, is adjacent the distal end of the ultrasound probe and that is in communication with the at least one force sensor, wherein the upper and lower members are configured to translate relative to each other while holding the ultrasound probe during the ultrasound evaluation so that (i) the adaptor body has first configuration that positions the at least one distalmost segment of the lower member forward of the distal end of the ultrasound probe and (ii) the adaptor body has a second configuration that positions the at least one distalmost segment a distance closer to the upper member relative to the first configuration, wherein, in the second configuration, a skin contacting portion of the distal end of the probe and the skin contacting portion of the lower member concurrently contact skin of the patient.

2. The adaptor of claim 1, wherein the adaptor further Comprises a plurality of spaced apart resilient members held by the first and second members of the adaptor body that, in operation, are able to change in length or elastically deform such that the resilient members translate from a first longer length or shape to a second shorter compressed length or shape when the probe applies compressive force to the target tissue.

3. The adaptor of claim 1, wherein the lower member has a distal end that extends about a perimeter of the distal end of the probe and has a laterally extending width of between 0.1 and 0.5 inches that defines the at least one distalmost segment.

4. The adaptor of claim 1, wherein the adaptor body comprises a ease that substantially encloses at least one side of the probe body, the adaptor body holding a plurality of spaced apart translating members that retract or compress in response to inward compression of the target tissue by the ultrasound probe.

5. The adaptor of claim 1, further comprising a plurality of translating members held by the adaptor body, the translating members reciprocate in response to manual inward compression and outward release of compression of the target tissue by the ultrasound probe.

6. The adaptor of claim 1, wherein the probe skin contacting portion has a surface having a surface area, and wherein the at least one force sensor extends Orthogonal to a plane extending parallel to the probe distal end skin contacting surface and adjacent a long side of the probe above the distal end thereof.

7. The adaptor of claim 6, wherein the at least one force sensor is a plurality of spaced apart force sensors residing above the lower member, wherein the lower member surrounds the probe and allows the distal end of the ultrasound probe to extend therethrough to contact skin of a patient, wherein the lower member of the adaptor body has a bottom with an oval perimeter that surrounds the distal end of the probe and provides the at least one distalmost segment.

8. The adaptor of claim 1, in combination with a system comprising the adaptor and having at least one processor with a module that is in communication with the adaptor and the ultrasound probe that is configured to: (i) generate force measurement data to metadata of ultrasound images; (ii) generate a color Coded overlay or mask image of tissue stiffness based on stress and strain data; and (iii) compute stress, strain and Elastic Modulus, for each segmented region of the target tissue.

9. The adaptor of claim 1 in combination with a system comprising the adaptor and having at least one processor with a module that is configured to synchronize an ultrasound image with a force measurement by the adaptor, calculate a stress using the force measurement and a surface area of a distal end of the probe, identify a change in length from a baseline associated with an initial at rest or uncompressed tissue thickness length of the target tissue to a compressed tissue length associated with the applied force of the target tissue and calculate strain and Elastic Modulus of the target tissue.

10. The adaptor of claim 1, wherein the adaptor is in communication with a system comprising the adaptor and having at least one processor configured to generate a color coded overlay of tissue stiffness of the target tissue using force measurement data from the adaptor; and a display that is in communication with the at least one processor that shows the color coded overlay of tissue stiffness.

11. An adaptor for an ultrasound probe, comprising:
an adaptor body releasably attachable to an outer portion of an ultrasound probe, the adaptor comprising at least one force sensor configured to obtain a force measurement of force applied to target tissue by a respective ultrasound probe, wherein the adaptor body has a lower end with an open portion that allows a distal end of the ultrasound probe to extend therethrough to contact skin of a patient, and wherein the adaptor body has at least one segment that is adjacent the distal end of the probe that is in communication with the at least one force sensor and that is sized and configured to contact the skin of the patient when a user applies a force to the probe,
wherein the adaptor body comprises an open frame body with upper and lower substantially rigid members, the adaptor body holding a plurality of spaced apart upwardly extending rods, with opposing end portions thereof attached to the upper and lower substantially rigid members, at least one coil spring surrounding each rod and residing between the upper and lower substantially rigid members, wherein the at least one force sensor comprises an elongate flex sensor that extends substantially parallel to and adjacent the coil spring of at least one of the rods, and wherein the lower member is the at least one segment that is sized and configured to contact skin of a patient and translate toward the upper member thereby compressing the toil springs toward the upper member in response to inward compression of the target tissue by the ultrasound probe.

12. An ultrasound system, comprising:
an ultrasound probe having an body with an outer surface and having a distal end with a skin contacting portion adapted to contact skin of a patient during an ultrasound evaluation;
an adaptor releasably attachable to the outer portion of an ultrasound probe at a location above the distal end of the ultrasound probe so that the distal end of the ultrasound probe is laterally spaced apart from the adaptor, the adaptor comprising at least one force sensor configured to obtain a force measurement of force applied to target tissue by the ultrasound probe during the ultrasound evaluation, wherein the adaptor has cooperating upper and lower members that releasably hold the ultrasound probe, the lower member having a lower end with an open portion that allows the distal end of the ultrasound probe to extend therethrough laterally spaced apart from the adapter, wherein the lower member of the adaptor has a skin contacting surface that contacts the skin of the patient during the ultrasound evaluation and that is in communication with the at least one force sensor, wherein the upper and lower members are configured to translate relative to each other while holding the ultrasound probe during the ultrasound evaluation so that the adaptor moves from a first configuration to a second configuration that positions the distalmost segment closer to the upper member relative to the first configuration, wherein, in at least the second configuration, the skin contacting portion of the distal end of the probe and the skin contacting portion of the lower member concurrently contact skin of the patient during an ultrasound evaluation.

13. The system of claim 12, wherein the at least one force sensor is a plurality of transversely spaced apart force sensors held above the lower member by the upper member, wherein the lower member surrounds the probe and allows the distal end of the ultrasound probe to extend therethrough to contact skin of a patient, wherein the lower member has an open inner perimeter and a radially extending outer perimeter that defines the skin contacting portion.

14. The system of claim 12, wherein the upper and lower members each comprise an aligned internal circular aperture and the outer surface of the ultrasound probe extends through the aligned circular apertures, wherein the at least one force sensor is a plurality of circumferentially spaced apart force sensors positioned on opposing sides of the circular aperture of the upper member.

15. The system of claim 12, wherein the skin contacting portion of the adaptor body has an oval perimeter that surrounds the skin contacting portion of the distal end of the ultrasound probe.

16. An ultrasound assembly, comprising:
an ultrasound probe with a distal end with an outer wall and a skin contacting portion; and
an adaptor with an adaptor body having a distal end, wherein the adaptor holds the ultrasound probe so that the distal end of the adaptor body is laterally spaced apart from the outer wall of the ultrasound probe, wherein the distal end of the probe and the distal end of the adaptor can move relative to each other, the distal end of the adaptor body having a skin contacting surface, wherein the adaptor further comprises a plurality of spaced apart force sensors in communication with the skin contacting surface of the adaptor body and residing above the distal end of the adaptor body, and wherein the skin contacting portion of the distal end of the probe and the skin contacting portion of the adaptor concurrently contact skin of the patient during an ultrasound evaluation when a user applies a force of between about 0.25 and 5 lbf to the probe.

17. The assembly of claim 16, wherein the skin contacting portion of the adaptor body has an oval perimeter that surrounds the skin contacting portion Of the distal end of the ultrasound probe.

* * * * *

UNITED STATES PATENT AND TRADEMARK OFFICE
CERTIFICATE OF CORRECTION

PATENT NO. : 9,615,815 B2  
APPLICATION NO. : 14/034756  
DATED : April 11, 2017  
INVENTOR(S) : Kwartowitz et al.

Page 1 of 1

It is certified that error appears in the above-identified patent and that said Letters Patent is hereby corrected as shown below:

In the Specification

Column 7, Line 59: Please correct "(a) and strain (c)." to read -- (σ) and strain (ε). --

In the Claims

Column 17, Claim 2, Line 24: Please correct "Comprises a plurality" to read -- comprises a plurality --

Claim 4, Line 38: Please correct "comprises a ease" to read -- comprises a case --

Claim 6, Line 50: Please correct "extends Orthogonal to" to read -- extends orthogonal to --

Claim 8, Line 67: Please correct "color Coded overlay" to read -- color coded overlay --

Column 18, Claim 8, Line 2: Please correct "Elastic Modulus, for" to read -- Elastic Modulus for --

Claim 11, Line 49: Please correct "compressing the toil" to read -- compressing the coil --

Column 20, Claim 17, Line 29: Please correct "portion Of the" to read -- portion of the --

Signed and Sealed this  
Thirtieth Day of January, 2018

Joseph Matal  
*Performing the Functions and Duties of the*  
*Under Secretary of Commerce for Intellectual Property and*  
*Director of the United States Patent and Trademark Office*